United States Patent
Palander

[11] Patent Number: 5,985,669
[45] Date of Patent: Nov. 16, 1999

[54] METHOD AND APPARATUS FOR TREATMENT OF HUMAN OR ANIMAL CELL SAMPLES

[75] Inventor: Jari Palander, Mulgrave, Australia

[73] Assignee: Australian Biomedical Corporation, Ltd., Victoria, Australia

[21] Appl. No.: 08/875,042

[22] PCT Filed: Jan. 4, 1996

[86] PCT No.: PCT/AU96/00007

§ 371 Date: Oct. 3, 1997

§ 102(e) Date: Oct. 3, 1997

[87] PCT Pub. No.: WO96/21142

PCT Pub. Date: Jul. 11, 1996

[30] Foreign Application Priority Data

Jan. 5, 1995 [AU] Australia .................... PN0389

[51] Int. Cl.⁶ ............... G01N 1/28; G02B 21/34
[52] U.S. Cl. ............... 436/46; 436/54; 436/174; 436/180; 422/63; 422/100; 422/104
[58] Field of Search ................... 422/57, 58, 99, 422/102, 103, 104, 63, 100; 436/174, 809, 46, 54, 180

[56] References Cited

U.S. PATENT DOCUMENTS 4,526,445 7/1985 Wogoman ................ 359/398
4,790,640 12/1988 Nason ..................... 359/396

FOREIGN PATENT DOCUMENTS 0 291 153 11/1988 European Pat. Off. .
0 334 534 9/1989 European Pat. Off. .
62-245156 10/1987 Japan .
8503194 6/1987 Netherlands .

*Primary Examiner*—Long V. Le
*Attorney, Agent, or Firm*—Pillsbury Madison & Sutro Intellectual Property Group

[57] ABSTRACT

Apparatus for treatment of human or animal cell samples on a microscopic slide includes an element having a recessed face defined by rails which are adapted to slide on surface of the slide. An opening at the leading edge of the element has a bevelled edge and provides access to a cavity formed between the face and the surface of the slide when the rails bear on the slide. The slide is tilted slightly and a vacuum nozzle is arranged at the lower edge of the slide. An end stop may be clamped to the end of the slide opposite to the end where the nozzle is located and has a bevelled edge complimentary to the bevelled edge of the element for closing the opening. A method of spreading liquid over the surface and the sample involves placing the rails on the surface with the cavity displaced laterally from the sample and the face and surface parallel, dispensing the liquid onto the surface and moving the element relative to the surface whereby the liquid becomes trapped in the cavity, and is spread evenly over the sample. The method also involves removing excess liquid after incubation by exposing the cavity to the vacuum nozzle by sliding the element over the lower edge of the slide and allowing the nozzle to suck the excess liquid away. Further treatment liquid may be added adjacent to the opening during the suction process to provide a second treatment without exposing the sample to air between treatments.

17 Claims, 1 Drawing Sheet

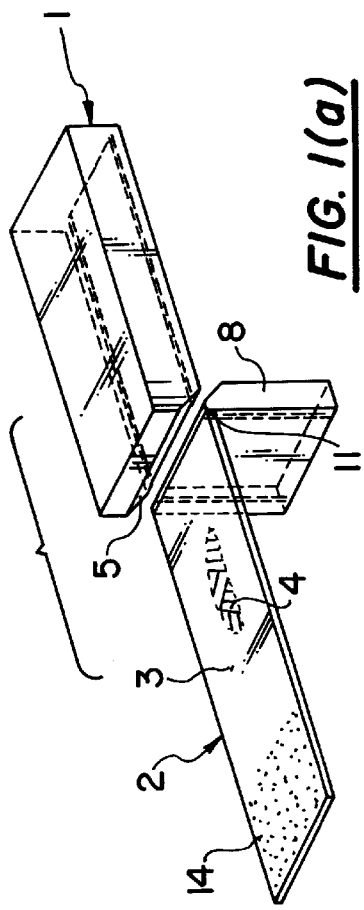
FIG. 1(a)
FIG. 1(b)
FIG. 1(c)
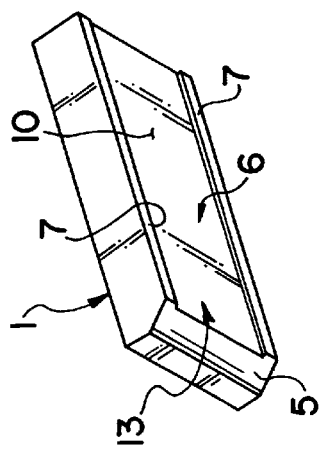
FIG. 3
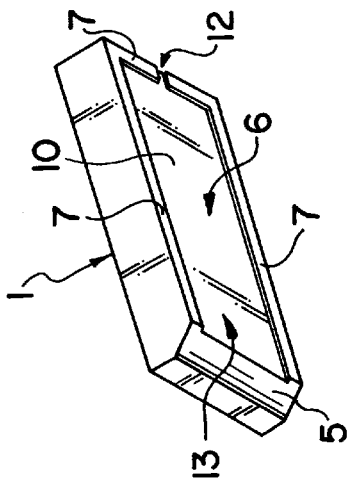
FIG. 2

5,985,669

METHOD AND APPARATUS FOR TREATMENT OF HUMAN OR ANIMAL CELL SAMPLES

BACKGROUND OF THE INVENTION

1. Field of the Invention

The present invention relates to a method and apparatus for treatment of human or animal cell samples. In particular, the invention relates to treatment of the samples to enable diagnosis of clinical conditions. A sample is fixed on a flat surface such as a microscope slide and chemically treated with liquid for the purpose of sample hydration or dehydration, or sample staining, or in chemical analysis such as detection of antigens or nucleic acid sequences, for example. The liquids used to treat such sample include:
1. Organic solvents.
2. Antibodies.
3. DNA and RNA probes.
4. Chemical solutions.
5. Washing solutions.

2. Description of the Related Art

Conventionally the chemical treatment and the chemical analysis of the samples is done by immersing the glass slides on which the samples are fixed into beakers that contain the treatment solutions. Certain solutions are expensive and they are dispensed onto a slide using a pipette with the slide in a horizontal orientation and a glass coverslip is placed on top of the slide to provide spread of the solution and to slow evaporation. The conventional process is labour intensive, exposes workers to reagent fumes and possibly to contact with the chemicals. Accurate timing of the processing steps can also be difficult to achieve. The amount of liquid waste generated is often large, which may be a problem, since the waste that needs to be disposed can contain aggressive solvents or biohazards such as infectious viruses. To overcome these problems a number of inventions have been proposed for automating the process.

In U.S. Pat. Nos. 4,731,335 and 4,777,020 and 5,002,736 Brigati, D. et al there is described a system where two flat surfaces such as microscope slides are placed face to face with sample sides facing inward. Abutting coating portions of the slides define a capillary gap between the samples. This slide pair can be placed so that the lower edge of the slide pair connects with the treating liquid which will then migrate into the capillary gap. Liquid can then be removed from the gap by placing the slide pair on top of and in contact with absorbent material which will drain and absorb the liquid.

Shandon Scientific Limited U.S. Pat. No. 4,985,206 describes an apparatus for processing tissue. The core of the invention is a channel-defining element. This element is joined together with a slide holding the sample with the sample side facing towards the element. The element forms a channel between its main wall and the slide. When the channel is substantially vertical the upper part of the element forms a liquid dispensing reservoir. An operator or a liquid handling robot can then fill the reservoir with appropriate reagent. Gravity and capillary action will cause the reagent to migrate into the channel. Once the channel is filled with liquid and the reservoir is empty, the liquid will stay in the gap due to surface tension of the liquid. The liquid in the gap can be replaced by placing new reagent in the reservoir.

Toya, M. et al in U.S. Pat. No. 5,068,091 and UK patent 2,265,981 describes a substantially horizontal wedge shaped capillary gap between a microscopic slide and lower plateau. Liquids can be dispensed to an exposed end of the plateau and capillary action will cause them to migrate to the wedge shaped gap. The gap can then be cleared of the reagent by using suction. Surface tension of the liquid will keep the liquid volume together during the removal process.

The aforementioned prior art apparatus all suffer a disadvantage in that they can in some instances fail to provide an even treatment of the sample with the treating liquid. This is caused by air becoming trapped in the capillary gap. In the case of the Brigati inventions, capillary forces can only lift the liquid a certain distance upwardly from the lower edge of the slide pair and this can lead to a reduced treatment area on the slide. The speed of liquid removal cannot be controlled in the Brigati inventions. The capillary gap also needs to be drained before a new liquid can be applied. These form a disadvantage, because in certain cases it is desirable that the samples are not exposed to air at all when replacing liquids. This is desirable especially when using volatile liquids such as organic solvents that evaporate easily and may let samples dry out during liquid replacement. Sample drying can lead to reduced processing quality such as high non-specific staining. In other cases a film of liquid should be left on the sample to keep it moist during liquid replacement. In the remaining cases it is desirable that the samples are dried completely before applying a new liquid to ensure maximum concentration of the applied liquid.

The apparatus of Shandon has the additional problem that no provision is made for clearing the gap (filling it with air) between different liquid treatments and therefore any air voids trapped in the gap are likely to remain through the process. Also the apparatus of Shandon cannot provide capability to expose the sample to air during processing while liquids are replaced. In the apparatus of Toya M. et al the suction to clear the capillary gap can lead to a breaking-up of the liquid into two or more sections with only one section being sucked into the waste containment system and such an incomplete clearing of the liquid can cause unacceptable treatment of the sample.

SUMMARY OF THE INVENTION

One object of the present invention may be to provide a method and an apparatus for spreading a small volume of liquid on a substantially flat surface supporting a human or animal cell sample, in a controlled manner whilst avoiding or at least reducing the possibility of any air gaps forming in the liquid spread. The range of liquids suitable for the invention include a wide range of viscosities and surface tensions.

Accordingly, the invention provides a method of spreading liquid onto a flat surface supporting a human or animal cell sample on part of the surface, characterised in that, said method comprises:
i) placing an element having a flat face adjacent said surface with the flat face parallel with, and in close proximity to, said surface and displaced laterally from said sample, said face being spaced at a defined distance from said surface by spacer means between said face and said surfaces;
ii) dispensing said liquid onto said surface or said element, and;
iii) after a required amount of liquid is dispensed, moving said element relative to said surface, whilst in contact with said surface via said spacer means, until the flat face of the element covers said sample, whereby said liquid becomes trapped in a cavity between the surface and the flat face and is spread evenly over said sample.

According to a further form of the invention, there is provided an apparatus for spreading liquid onto a flat surface containing a human or animal cell sample on part of the surface, characterised in that, said apparatus comprises an element having a slightly recessed flat face whereby when said element is placed on said surface with said face parallel to said surface a thin cavity is defined between said element and said surface, said cavity is accessible along one edge of said element and said cavity is of sufficient size to accommodate said sample.

BRIEF DESCRIPTION OF THE DRAWINGS

In order that the invention may be more readily understood a particular embodiment will now be described with reference to the accompanying drawings wherein:

FIGS. 1a–1c shows in three separate views (FIG. 1a), (FIG. 1b) and (FIG. 1c) a perspective of a microscopic slide and associated element of the invention in different relative positions and views (FIG. 1b) and (FIG. 1c) include an end stop on the slide;

FIG. 2 is a perspective underside view of the elements of FIGS. 1a–1c in one particular form; and FIG. 3 is a similar view to FIG. 2 showing an alternative embodiment of the element.

DETAILED DESCRIPTION OF THE INVENTION

Referring to FIG. 1, there is shown a substantially flat element 1 and a sample carrying microscopic slide 2. The microscopic slide 2 has a sample carrying or supporting surface 3 on which a sample 4 is to be placed and the flat element 1 has a bevelled edge 5 on one end, defining an opening into a recess or cavity 6 (FIG. 2) formed in a face of the element.

In use, after the sample 4 has been placed on the sample carrying surface 3 of the slide, the flat element 1 and the slide are arranged such that a planar base 10 of the recess 6 and the sample carrying surface 3 are generally parallel to each other with the recess 6 and the sample carrying surface 3 generally facing each other, and such that they are laterally offset from each other with the bevelled edge 5 of the element 1 covering an end portion of the slide 2 adjacent a transverse edge 11 (similar to the position shown in FIG. 1(a)). It is preferable, but not essential, that the planar base 10 of the recess 6 and the sample carrying surface 2 are spaced from each other by a distance of about 20 micrometres to 300 micrometres.

The first of a number of treatment liquids (not shown) is then dispensed directly onto the sample 4, or onto the sample carrying surface 3 at a location between the bevelled edge 5 of the element and the sample 4. The element 1 is then moved in a direction towards the sample so that an opening 13 into the recess 6 passes over the sample while the defined distance between the base 10 of the recess 6 and the sample carrying surface 3 is maintained whereby the sample 4 and a major portion of the treatment liquid are trapped within the recess 6.

In some instances, it may be desirable to move the element 1 back and forth on the slide 2 to provide agitation to the liquid before and/or during the incubation process. This agitation can result in a better penetration of the treatment liquid into the sample and thus provide an improved result.

The planar base 10 of the recess 6 is preferably larger than the treated area of the sample 4 carried by the flat surface 3, but smaller than the flat surface itself.

It may be preferable to retain a small amount of the treatment liquid on the sample after the sample has incubated to avoid the sample drying out before the next treatment liquid is applied.

After the sample incubation period has ended, the excess treatment liquid is removed from the sample carrying surface 3 to enable application of the next treatment liquid. This can be done at the same time as the element 1 is retracted along the length of the slide to again expose the sample 4.

As the volume defined between the sample carrying surface 3 and the base 10 diminishes during the reverse movement of the element, that is, as the volume of the recess or cavity 6 decreases, the surface tension of the liquid acts to keep the liquid as a single entity. To remove the excess liquid that does not fit into the diminishing volume, a vacuum nozzle 8 is arranged at the transverse edge 11 of the sample carrying surface 3 such that the nozzle 8 faces the recess 6 and is in close proximity to it. As the element 1 is retracted and moves past the nozzle, the excess treatment liquid is removed from the element 1 by an applied vacuum and is filled into a closed container (not shown) since it could otherwise present an environmental risk. Once the excess liquid for the first treatment has been removed, a second treatment liquid can be dispensed for subsequent incubation, and the process repeated for further treatment liquids as required.

The relative movement of the element 1 and slide 2 can be automated and controlled by a computer (not shown). Since the mechanism does not form part of the present invention it is not considered necessary to describe it herein other than to say that in one form a belt driven linear axis driven by a microstepping step motor is used. Further, this relative movement may be conducted in multiple stages. For example, in the first stage the element may be moved to only partially cover the surface, then halted for a period of time to allow the treatment liquid to fill the space between the bevelled edge 5 of the element 1 and the transverse edge 11 of the slide to minimize the likelihood of air becoming trapped within the recess 6 on completion of the relative movement. In the second stage, the relative movement may be continued again ensuring that any air originally within the recess has been wholly replaced by the sample 4 and the treatment liquid.

Referring now to FIG. 2 which shows one form of the element 1, the recess comprises a substantially flat surface 10 on the element 1 having three outwardly extending protrusions, or rails 7. The rails 7 are arranged in a general "U-shape" which, with the flat base surface 10 on the element 1, defines a recess which is open at one short edge only. This means that in use the recess virtually fully encloses the sample 4. The reason for the recess substantially enclosing the sample 4 is to reduce the evaporation rate of the liquid when trapped in the recess. This is advantageous during prolonged high temperature incubations requiring several treatment processes.

The rail 7 at the other short end of the recess 6 may have a small opening 12 formed in it to allow air to escape from the recess during the relative movement of the element 1 and the slide 2. Alternatively, the rail at the closed end of the recess 6 may be removed altogether as is shown in the alternative embodiment of FIG. 3.

In a further alternative, other means may be provided on the element 1 or on the slide 2 to maintain the desired spacing therebetween. Such means could, for example, comprise small bosses or protrusions extending outwardly from the face of the element 1 or from the sample carrying flat surface 3 of the slide 2.

In order to further reduce evaporation of the treatment liquid during incubation, an end stop 9 can be clamped, for example, onto the slide 2 to restrict or close the opening to the recess at the bevelled edge 5 of the element 1. The end stop 9 should be positioned such that it engages the end of the element at the bevel when the element has moved to its final incubation position and for this purpose the end stop 9 has a bevelled edge complimentary to the bevelled edge 5 of the element 1. In some instances, it is especially beneficial to the process to add the second or further treatment liquids to the recess 6 without exposing the sample to the air. The reason for this is that exposing the sample to the air may lead to drying of the sample which can reduce the quality of the treatment. This is especially so with some staining procedures.

If air is to be excluded, the current treatment liquid can be replaced by a further treatment liquid by moving the element 1 slightly so that the recess 6 is just open to the vacuum nozzle, then applying vacuum while concurrently dispensing the further treatment liquid onto the sample carrying surface 3. In other words only a small part of the recess or cavity 6 is exposed. It is preferable, in this case, that the further liquid be dispensed at the opposite end of the element to the vacuum nozzle. In practice, the excess of the further treatment liquid tends to migrate to the recess due to the cohesive forces of the liquid while the liquid is under vacuum and will be captured by the vacuum nozzle. The migration of the liquid substantially stops once the excess treatment liquid at the dispensing end is used up.

This process can be facilitated by orienting the whole arrangement at an angle, preferably about 5°, with the vacuum nozzle being at the lower end of the surface and the dispensing of further liquid being at the upper end of the surface.

It is preferable that the element 1 has a thickness which is sufficient to prevent treatment liquids dispensed onto the sample 4 flowing over the top of the element during the relative movement. Typically, this thickness will be more than 2 mm. In addition, the bevelled edge 5 can be angled at various different angles relative to the plane of the surface 3 to allow the element to rise above any obstacles on the slide, for example wax granules on a paraffin fixed sample.

It is preferable that the element 1 be formed of a chemically inert material, so that it does not affect the treatment reactions, and that it be manufactured of a material that withstands organic solvents to allow, for example, dewaxing and dehydration procedures to be conducted on the sample. It is also desirable that the element be manufactured of a transparent or translucent material to enable a user to observe the reaction taking place in the sample. To satisfy all of these requirement the element is preferably formed of glass, and the rails or protrusions are printed or painted onto the element using an inert and durable material such as a Fluoro Ethylene Polymer. Alternatively, the rails may also be formed of glass using various manufacturing processes such as grinding or etching.

If the sample carrying surface is a microscope slide the vacuum nozzle can be placed at the end of the slide that is closest to the sample area. This end is typically opposite to a frosted end 14 of the slide. In a preferred form, the opening of vacuum nozzle can be in the form of slit which may be substantially the same width as that of the microscope slide and it can be aligned such that the slit length is parallel to the face of the microscope slide.

I claim:

1. A method of spreading liquid onto a flat surface supporting a human or animal cell sample on a portion of the surface, said method comprising the steps of:

i) placing an element having a flat face adjacent the surface so that the flat face is parallel with, in close proximity to, and displaced laterally from the sample, the flat face being spaced at a defined distance from the surface by space means;

ii) dispensing the liquid onto the surface or the element; and iii) after said step of dispensing the liquid, moving the element relative to the surface, while the element is in contact with the surface via the spacer means, until the flat face of the element covers the sample and the liquid becomes trapped in a cavity defined between the surface and the flat face and is spread evenly over the sample.

2. A method according to claim 1, said method further comprising steps of:

removing excess amounts of the liquid after suitable incubation of the sample; and moving the element, relative to the surface, in a direction away from the sample while maintaining contact between the element and the surface and, as the cavity moves over an end of the surface, applying a vacuum at the end to remove the excess liquid which is held in the cavity by surface tension of the liquid.

3. A method according to claim 2, further comprising applying a further treatment liquid to the sample to replace the removed excess liquid without exposing the sample to air, wherein said step of moving the element in a direction away from the sample comprises moving the element only sufficiently to expose a small part of the cavity to the vacuum, and wherein said step of applying the further treatment liquid is conducted concurrently with said step of applying the vacuum, the further liquid being applied adjacent an opposite end of the element to the end at which the vacuum is applied.

4. A method according to claim 3, said method further comprising inclining the surface and the element at a slight angle to the horizontal, wherein said step of applying the vacuum comprises applying the vacuum to a lower end of the surface.

5. A method according to claim 1, wherein said method further comprises moving the element back and forth on the surface and thereby agitating the liquid before and/or during an incubation process.

6. A method according to claim 1, wherein said step of dispensing liquid onto the surface or the element comprises dispensing the liquid onto the surface adjacent an opening to the cavity.

7. An apparatus for spreading liquid onto a flat surface supporting a human or animal cell sample on a portion of said surface, said apparatus comprising an element having a slightly recessed flat face constructed and arranged such that, when said element is placed on said surface with said face parallel to said surface, a thin cavity is defined between said element and said surface, wherein said cavity is accessible along one edge of said element and said cavity is of sufficient size to accommodate said sample, and wherein relative movement between said element and said surface is automated and controlled by a computer.

8. An apparatus according to claim 7, wherein said element further comprises a plurality of raised rails, and wherein said cavity is defined by said flat surface, said flat face parallel to said surface, and said raised rails on said flat surface, wherein said raised rails respectively extend generally along two parallel edges of said element, and wherein said one edge which provides access to said cavity does not have a rail.

9. An apparatus according to claim 8, wherein said flat surface is on a microscopic slide, and wherein said apparatus further includes a vacuum nozzle arranged below and adjacent an edge of said slide.

10. An apparatus according to claim 9, wherein said one edge of said element which provides access to said cavity is a bevelled edge which forms an acute angle relative to said surface when said element is placed on said surface.

11. An apparatus according to claim 10, wherein said apparatus further comprises an end stop for clamping onto said slide, said end stop engaging said bevelled edge of said element when said element is in a final incubation position on said slide, said end stop having a bevelled edge complimentary to said bevelled edge of said element for closing access along said bevelled edge of said element in said final incubation position of said element.

12. An apparatus according to claim 7, wherein said relative movement is conducted in stages whereby in a first stage said element is moved from a first position in which said bevelled edge of said element is adjacent an end portion of said slide to a second position in which said element partially covers said surface and remains in the second position for a period of time sufficient to allow treatment liquid, placed on said surface prior to said first stage, to fill a space defined between said bevelled edge of said element and said end portion of said slide, and in a second stage the element is moved further over said slide such that the sample is contained within said cavity and any air originally contained within said cavity is wholly displaced by said sample and said treatment liquid.

13. An apparatus according to claim 12, wherein said slide and said element are inclined at a slight angle to the horizontal and said vacuum nozzle is at a lower edge of said slide.

14. An apparatus according to claim 13, wherein said automated and controlled relative movement between said slide and said element is adapted to move said element back and forth relative to said slide to promote agitation of said liquid before and/or during the incubation process.

15. An apparatus according to claim 13, wherein said element including said rails is formed of glass and each of said rails has a height above said flat face that is between 20 and 150 micrometers.

16. An apparatus according to claim 13, wherein said element is formed of glass with the exception of said rails, which are printed or painted thereon using an inert and durable material, and wherein each of said rails has a height above said flat face that is between 20 and 300 micrometers.

17. A method according to claim 1, wherein said moving step comprises controlling a distance between the surface and said flat face of said element with a computer.

* * * * *